United States Patent
Kim et al.

(10) Patent No.: US 8,877,538 B2
(45) Date of Patent: Nov. 4, 2014

(54) PRESSURE SENSOR HAVING NANOSTRUCTURE AND MANUFACTURING METHOD THEREOF

(71) Applicant: Korea Institute of Science and Technology, Seoul (KR)

(72) Inventors: Jin Seok Kim, Seoul (KR); Jun-Kyo Francis Suh, Seoul (KR); Sung Chul Kang, Seoul (KR); Jeong Hoon Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/686,375

(22) Filed: Nov. 27, 2012

(65) Prior Publication Data

US 2013/0140611 A1    Jun. 6, 2013

(30) Foreign Application Priority Data

Dec. 5, 2011  (KR) .................. 10-2011-0128939

(51) Int. Cl.
| | | |
|---|---|---|
| H01L 21/00 | (2006.01) | |
| A61B 5/03 | (2006.01) | |
| H01L 29/66 | (2006.01) | |
| H01L 29/84 | (2006.01) | |
| B82Y 15/00 | (2011.01) | |
| G01L 7/08 | (2006.01) | |
| B82Y 99/00 | (2011.01) | |

(52) U.S. Cl.
CPC ............... *H01L 29/84* (2013.01); *A61B 5/031* (2013.01); *H01L 29/66007* (2013.01); *A61B 2562/0247* (2013.01); *A61B 2562/046* (2013.01); *B82Y 15/00* (2013.01); *B82Y 99/00* (2013.01); *G01L 7/08* (2013.01); *Y10S 977/956* (2013.01); *Y10S 977/90* (2013.01); *Y10S 977/936* (2013.01)
USPC .................. 438/53; 438/50; 438/49; 257/254; 257/252; 257/253; 977/956; 977/900; 977/936

(58) Field of Classification Search
USPC ........ 257/254, 252, 253, 417; 438/53, 50, 49; 977/936, 956, 900
See application file for complete search history.

(56) References Cited

U.S. PATENT DOCUMENTS

| 7,644,622 B2 | 1/2010 | Qiao et al. | |
|---|---|---|---|
| 7,683,323 B2 * | 3/2010 | Kymissis ................... | 250/338.3 |

(Continued)

FOREIGN PATENT DOCUMENTS

| JP | 2003-227808 A | 8/2003 |
|---|---|---|
| JP | 2004-053424 A | 2/2004 |

(Continued)

OTHER PUBLICATIONS

Stefan C.B. Mannsfeld et al., "Highly Sensitive Flexible Pressure Sensors With Microstructured Rubber Dielectric Layers," Nature materials, vol. 9, Oct. 2010, pp. 859-864 (6 pages, in English).

(Continued)

*Primary Examiner* — Timor Karimy
(74) *Attorney, Agent, or Firm* — NSIP Law

(57) ABSTRACT

The present disclosure relates to a pressure sensor having a nanostructure and a method for manufacturing the same. More particularly, it relates to a pressure sensor having a nanostructure attached on the surface of the pressure sensor and thus having improved sensor response time and sensitivity and a method for manufacturing the same. The pressure sensor according to the present disclosure having a nanostructure includes: a substrate; a source electrode and a drain electrode arranged on the substrate with a predetermined spacing; a flexible sensor layer disposed on the source electrode and the drain electrode; and a nanostructure attached on the surface of the flexible sensor layer and having nanosized wrinkles.

9 Claims, 14 Drawing Sheets

(56) References Cited

U.S. PATENT DOCUMENTS

| | | |
|---|---|---|
| 2006/0288774 A1 | 12/2006 | Jacob et al. |
| 2007/0210349 A1* | 9/2007 | Lu et al. ................ 257/252 |
| 2010/0126273 A1 | 5/2010 | Lim et al. |

FOREIGN PATENT DOCUMENTS

| | | |
|---|---|---|
| JP | 2005-279807 A | 10/2005 |
| JP | 2009-198337 | 9/2009 |
| JP | 2010-199298 A | 9/2010 |
| JP | 2011-196740 | 10/2011 |
| KR | 10-2007-0042746 A | 4/2007 |
| KR | 10-2010-0074909 A | 7/2010 |

OTHER PUBLICATIONS

Hyun-Ju Choi, et al., "A Study on Mechanical Characterization of Nano-Thick Films Fabricated by Transfar Assembly Technique," The Korean Society of Mechanical Engineers, the collection of dissertations of Autumn Conference 2008, pp. 30-34 (5 pages, including English language abstract).

* cited by examiner

FIGURE

PRESSURE SENSOR HAVING NANOSTRUCTURE AND MANUFACTURING METHOD THEREOF

CROSS-REFERENCE TO RELATED APPLICATION

This application claims priority to Korean Patent Application No. 10-2011-0128939, filed on Dec. 5, 2011, and all the benefits accruing therefrom under 35 U.S.C. §119, the contents of which in its entirety are herein incorporated by reference.

BACKGROUND

1. Field

The present disclosure relates to a pressure sensor having a nanostructure and a method for manufacturing the same. More particularly, it relates to a pressure sensor having a nanostructure attached on the surface of the pressure sensor and thus having improved sensor response time and sensitivity and a method for manufacturing the same.

2. Description of the Related Art

A pressure sensor is a device used to measure pressure of liquids or gases and converts the measurement result into an electrical signal that can be processed or controlled easily.

Recently, as the pressure sensor is used for brain surgery, higher response time and sensitivity are required for the pressure sensor. During the brain surgery, measurement of intracranial pressure is very important since the intracranial pressure is closely related with hemorrhages and complications. Therefore, a pressure sensor capable of sensitively responding to a small change in the intracranial pressure is required.

Various methods are presented to improve the sensitivity of the pressure sensor. FIG. 1 shows an ITO/PET film having a microstructure which is attached on an existing pressure sensor.

Referring to FIG. 1, an ITO/PET film having a microstructure is fabricated using a silicon mold. The ITO/PET film is attached on a pressure sensor to improve the sensitivity of the pressure sensor.

However, the fabrication of the ITO/PET film using the silicon mold is restricted for a microsized structure. That is to say, it is not applicable to a smaller, nanosized structure. When a nanosized structure is introduced to the pressure sensor, the response time and sensitivity of the pressure sensor may be further improved.

REFERENCES CITED

Non-Patent Documents

Non-patent document 1: Highly sensitive flexible pressure sensors with microstructured rubber dielectric layers, Stefan C. B. Mannsfeld et al., *Nature Materials*, Vol. 9, October 2010, pp. 859-864.

SUMMARY

The present disclosure is directed to providing a pressure sensor having a nanostructure attached on the surface of the pressure sensor and thus having improved sensor response time and sensitivity and a method for manufacturing the same.

In one general aspect, the present disclosure provides a pressure sensor including: a substrate; a source electrode and a drain electrode arranged on the substrate with a predetermined spacing; a flexible sensor layer disposed on the source electrode and the drain electrode; and a nanostructure attached on the surface of the flexible sensor layer and having nanosized wrinkles.

The nanostructure may be a linear 1-dimensional structure, a zigzag-shaped 2-dimensional structure or a spiral-shaped structure.

The pressure sensor may further include a dome structure attached on the surface of the nanostructure to maximize pressure sensing in a 3-dimensional direction.

The dome structure dome structure may be formed of PDMS, PMMA, SU8, PU, parylene or elastomer.

The flexible sensor layer may be formed of thin-film PVDF, flexible thin-film piezoelectric PZT, or rubrene crystal.

The nanostructure may be formed of a polymer material.

In another general aspect, the present disclosure provides a method for manufacturing a pressure sensor, including: arranging a source electrode and a drain electrode on a substrate; disposing a flexible sensor layer on the source electrode and the drain electrode; forming nanosized wrinkles on a thin film of a polymer material to prepare a nanostructure; and attaching the nanostructure having wrinkles on the surface of the flexible sensor layer.

The preparing the nanostructure may include forming a linear 1-dimensional structure.

The forming the linear 1-dimensional structure may include forming wrinkles by disposing a mask on the thin film, applying UV ozone (UVO) or $O_2$ plasma to modify the surface selectively exposed by the mask and forming wrinkles using the difference in stress between the modified surface and the unmodified surface, while applying tension to the thin film.

The forming the linear 1-dimensional structure may include forming wrinkles on the portion of the thin film having a relatively smaller thickness by applying tension and UVO.

The preparing the nanostructure may include forming a zigzag-shaped 2-dimensional structure.

The forming the zigzag-shaped 2-dimensional structure may include artificially depositing a nano-linewidth metal thin film or metal oxide thin film having tensile strength on the thin film of a polymer material and artificially removing the metal thin film or the metal oxide thin film to generate local stress, thus forming wrinkles.

The preparing the nanostructure may include forming a spiral-shaped structure.

The forming the spiral-shaped structure may include applying tensile strength to both ends of the thin film, masking the portion except for the portion where wrinkles will be formed using a PET film or a photoresist, modifying the surface using UVO and removing the tensile strength applied to the thin film to form the wrinkles.

The forming the spiral-shaped structure may include masking the thin film with a PET film or a photoresist, artificially depositing a nano-linewidth metal thin film or metal oxide thin film having tensile strength on the thin film and artificially removing the metal thin film or the metal oxide thin film to generate local stress, thus forming wrinkles.

The method for manufacturing a pressure sensor may further include forming a nanosized dome structure and attaching it on the nanostructure having wrinkles.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION OF MAIN ELEMENTS

Figure 1:
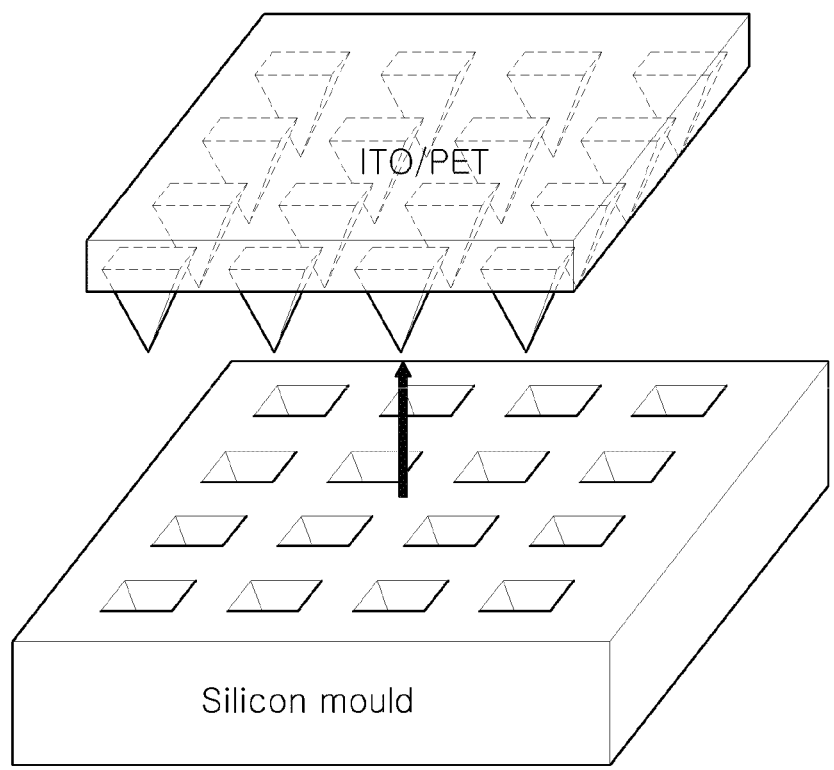
FIG. 1 shows an ITO/PET film having a microstructure which is attached on an existing pressure sensor.

100: pressure sensor
110: substrate
120: source electrode
130: drain electrode
140, 640: flexible sensor layer
150, 250, 350, 360, 650: nanostructure
152, 252, 352, 362, 652: wrinkles
410, 510, 610: thin film
412: wrinkles
420, 430: mask
510a, 510c: thick portion
510b: thin portion
512: wrinkles
620: PET film
622: spiral-shaped through-hole
660: dome structure

DETAILED DESCRIPTION

Hereinafter, a pressure sensor having a nanostructure and a method for manufacturing the same according to exemplary embodiments of the present disclosure will be described in detail with reference to the accompanying drawings.

FIGS. 2a-2e show a pressure sensor according to an exemplary embodiment of the present disclosure.

Referring to FIGS. 2a-2e, a pressure sensor 100 according to an exemplary embodiment of the present disclosure comprises a substrate 110, a source electrode 120, a drain electrode 130, a flexible sensor layer 140 and a nanostructure 150, 250, 350, 360.

The source electrode 120 and the drain electrode 130 are arranged on the substrate 110 with a predetermined spacing. A pressure input to the flexible sensor layer 140 is converted into an electrical signal by the electrodes.

The flexible sensor layer 140 is disposed on the source electrode 120 and the drain electrode 130. The flexible sensor layer 140 may be prepared, for example, from a piezoelectric polymer material such as thin-film polyvinylidene difluoride (PVDF), flexible thin-film PZT, or rubrene crystal.

Figure 2A:
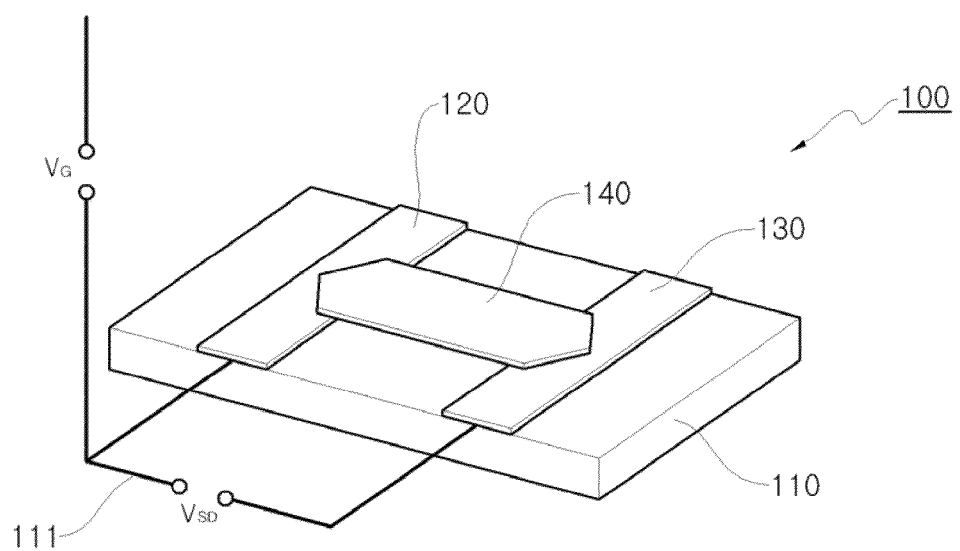
FIGS. 2a-2e show a pressure sensor according to an exemplary embodiment of the present disclosure.

The nanostructure 150, 250, 350, 360 having nanosized wrinkles shown in FIGS. 2b-2e is attached on the flexible sensor layer 140 shown in FIG. 2a. As the nanostructure 150, 250, 350, 360 is attached integrally to the flexible sensor layer 140, the sensitivity and response time of the pressure sensor 100 may increase greatly.

The nanostructure 150, 250, 350, 360 may be formed into various shapes and each of the nanostructure 150, 250, 350, 360 has a plurality of wrinkles 152, 252, 352, 362.

Figure 2B:
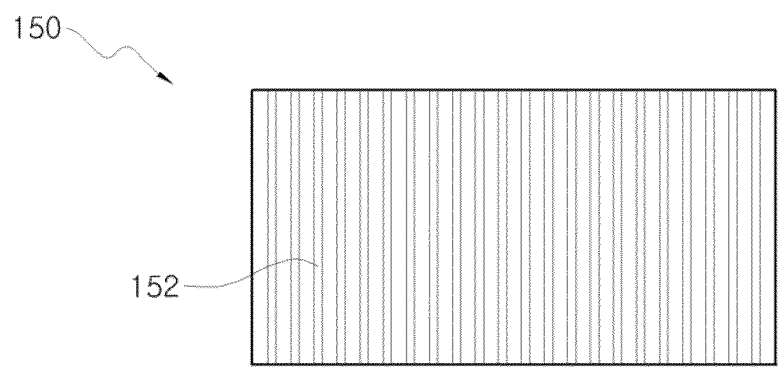

In FIG. 2b, the nanostructure 150 is a linear 1-dimensional structure and a plurality of wrinkles 152 are formed linearly in parallel.

Figure 2C:
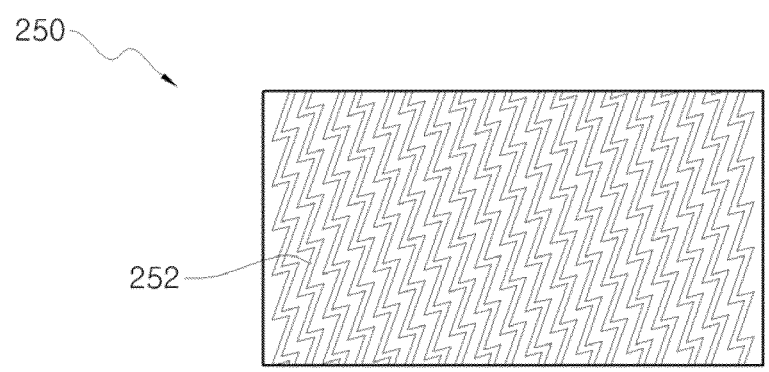
Figure 2D:
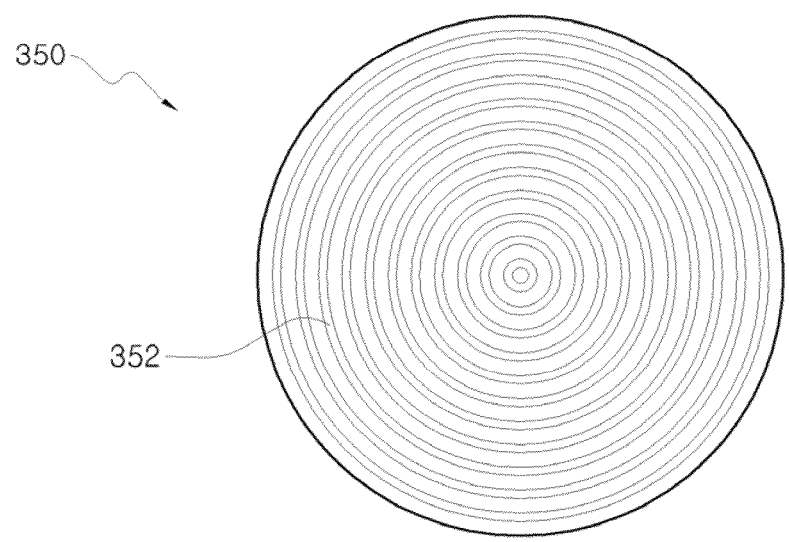
Figure 2E:
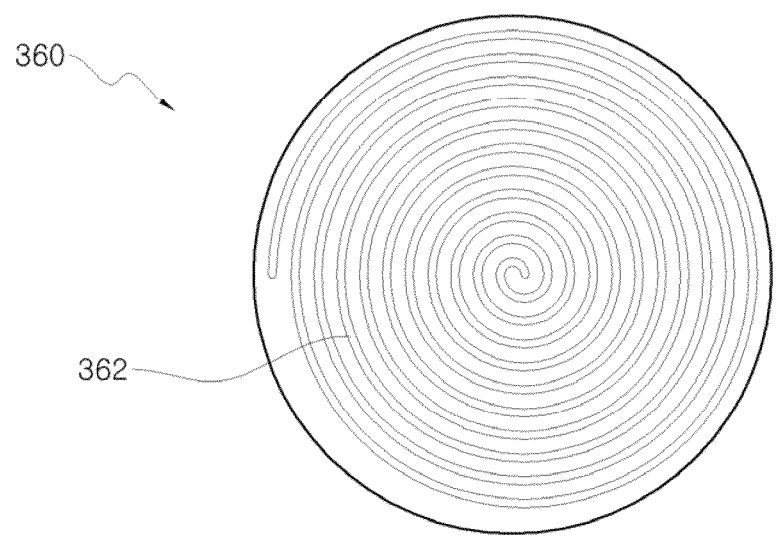

In FIG. 2c, FIG. 2d and FIG. 2e, the nanostructure 250, 350, 360 is a zigzag-shaped 2-dimensional structure or a spiral-shaped structure. The nanostructure 250, 350, 360 of FIG. 2c, FIG. 2d, FIG. 2e may respond more sensitively to pressure change than the nanostructure 150 of FIG. 2b because of their structural shape.

Figure 3A:
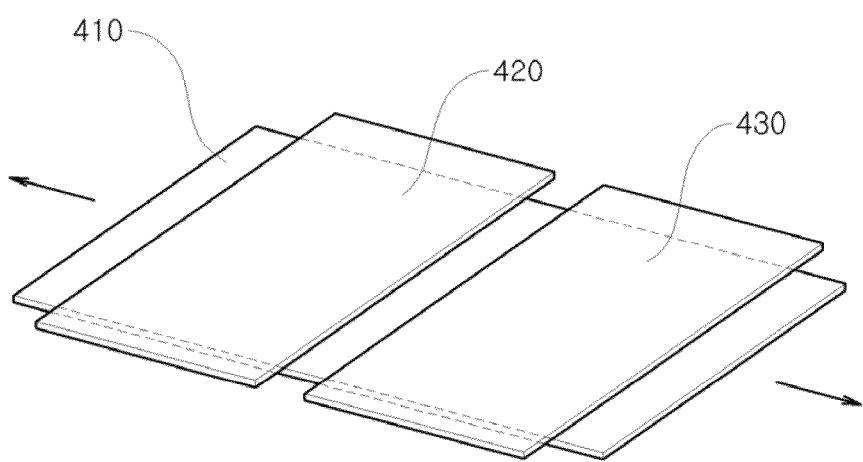
FIGS. 3a-3b illustrate a method of forming the wrinkles of the nanostructure of FIG. 2b.
Figure 3B:
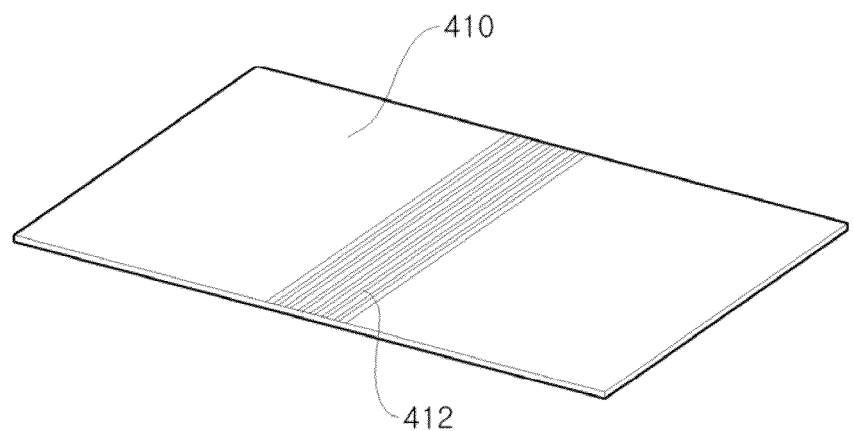

FIGS. 3a-3b illustrate a method of forming the wrinkles of the nanostructure of FIG. 2b.

Referring to FIG. 3a, a transparent mask 420, 430 is disposed on a thin film 410 and UV ozone (UVO) or $O_2$ plasma is applied while applying tension to both ends of the thin film 410. Then, the surface selectively exposed by the mask 420, 430, i.e. the intermediate portion of FIG. 3a, is modified and wrinkles 412 are formed in the middle portion as shown in FIG. 3b due to the difference in stress between the modified middle portion and the portion protected by the mask 420, 430.

If the thin film 410 is partially cut around the portion having the wrinkles 412 formed, the nanostructure 150 shown in FIG. 2b may be obtained. The thin film 410 may comprise a polymer material that can be easily processed with heat and pressure.

Figure 4A:
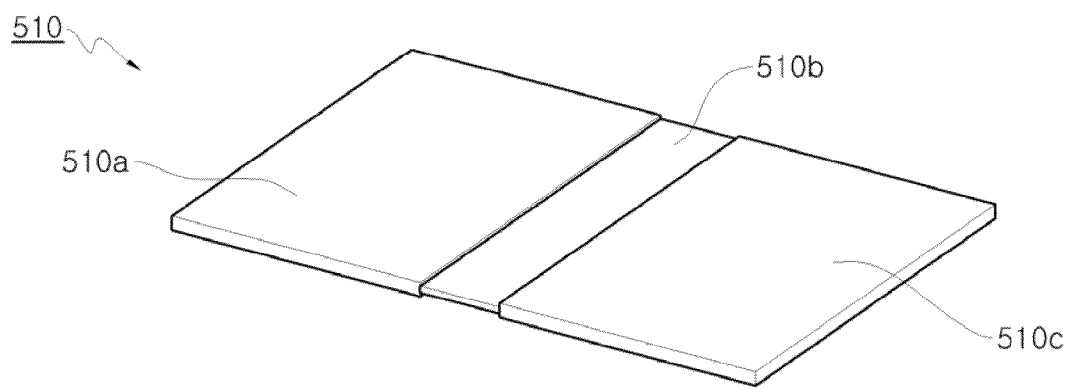
FIGS. 4a-4c illustrate another method of forming the wrinkles of the nanostructure of FIG. 2b.
Figure 4B:
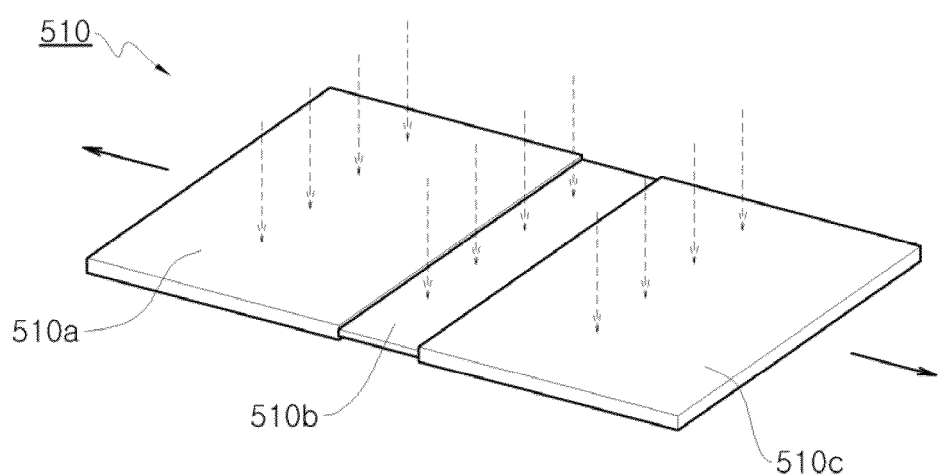
Figure 4C:
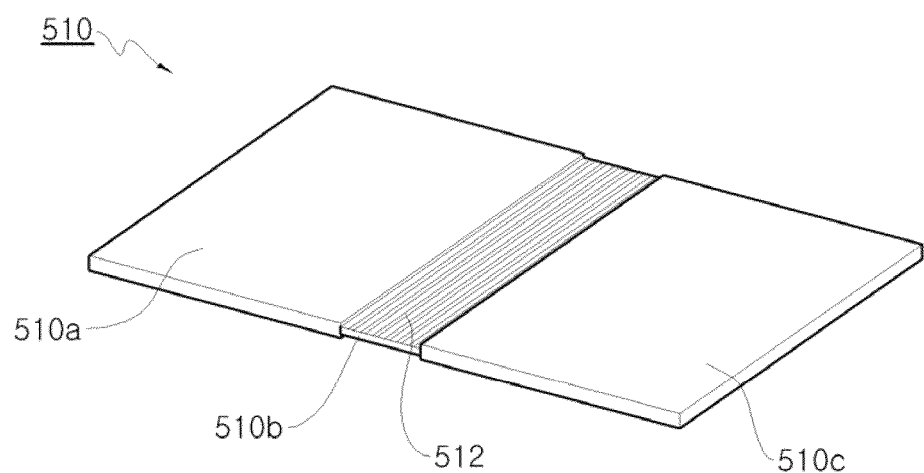

FIGS. 4a-4c illustrate another method of forming the wrinkles of the nanostructure of FIG. 2b.

Referring to FIG. 4a, a thin film has a relatively thick portion 510a, 510c and a relatively thin portion 510b. Although a mask is used in the embodiment illustrated in FIGS. 3a-3b, in this embodiment, UVO is applied from above the thin film while applying tension to both ends of the thin film as shown in FIG. 4b, without using a mask.

Difference in stress occurs between the portions having different thickness due to the tension and UVO treatment. As a result, wrinkles 512 are formed in the thin portion 510b which is relatively vulnerable to the stress as shown in FIG. 4c.

Meanwhile, the nanostructure 250 having the zigzag-shaped wrinkles 252 as shown in FIG. 2c may be formed by wrinkling alike the linear structure or by buckling. The buckling refers to a process of artificially depositing a nano-linewidth metal thin film or metal oxide thin film having external tension, usually tensile strength, on a substrate and then artificially removing the metal thin film or the metal oxide thin film to generate local stress, thus forming wrinkles.

The zigzag-shaped wrinkles 252 enable transfer and sensing of not only normal pressure but also shear stress via 2-dimensional transfer of force and maximize the transfer of force in x-y directions.

And, the nanostructure 350, 360 having the spiral-shaped wrinkles 352, 362 as shown in FIG. 2d or FIG. 2e may be formed by wrinkling or buckling as described above.

Figure 5:
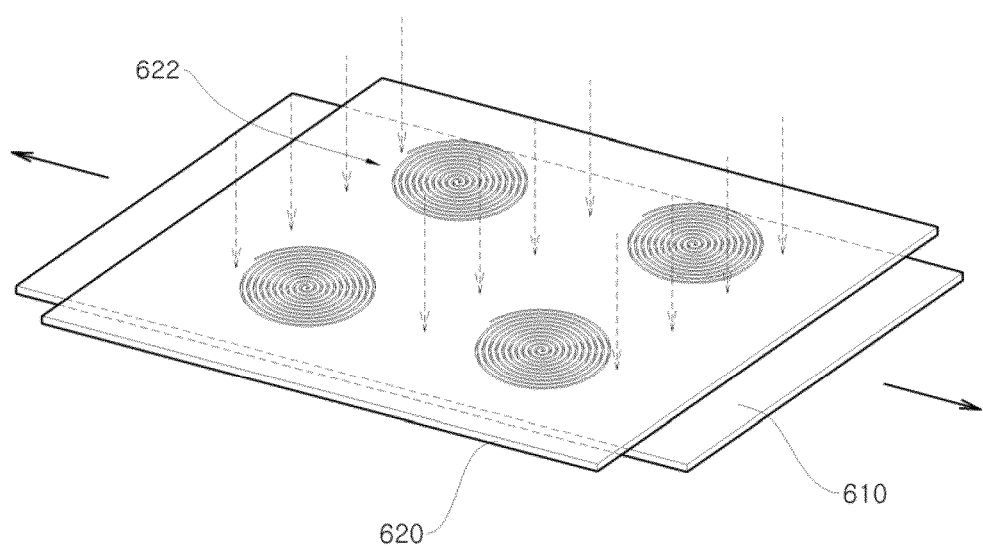
FIG. 5 illustrates a method of forming the wrinkles of the nanostructure of FIG. 2d or FIG. 2e.

FIG. 5 illustrates a method of forming the wrinkles of the nanostructure of FIG. 2d or FIG. 2e.

Referring to FIG. 5, in order to form the spiral-shaped wrinkles 352, 362, tensile strength is applied to a thin film 610 and the portion except for the portion where the wrinkles will be formed is masked using a PET film 620 or a photoresist. Then, after modifying the surface using UVO, the tensile strength applied to the thin film 610 is removed to form the nanowrinkles 352, 362. As the surface of the thin film 610 is exposed to UVO by a spiral-shaped through-hole 622 of the PET film 620, the nanowrinkles having a shape corresponding to the spiral-shaped through-hole 622 are formed.

Alternatively, after masking the thin film 610 with the PET film 620 or the photoresist, a nano-linewidth metal thin film or metal oxide thin film having external tension, usually tensile strength, may be artificially deposited on the thin film 610 and then the metal thin film or the metal oxide thin film may be artificially removed to generate local stress, thus forming wrinkles.

The spiral-shaped wrinkles 352, 362 enable transfer and sensing of not only normal pressure but also shear stress via 2-dimensional transfer of force and maximize the transfer of force in x-y-z directions.

Figure 6:
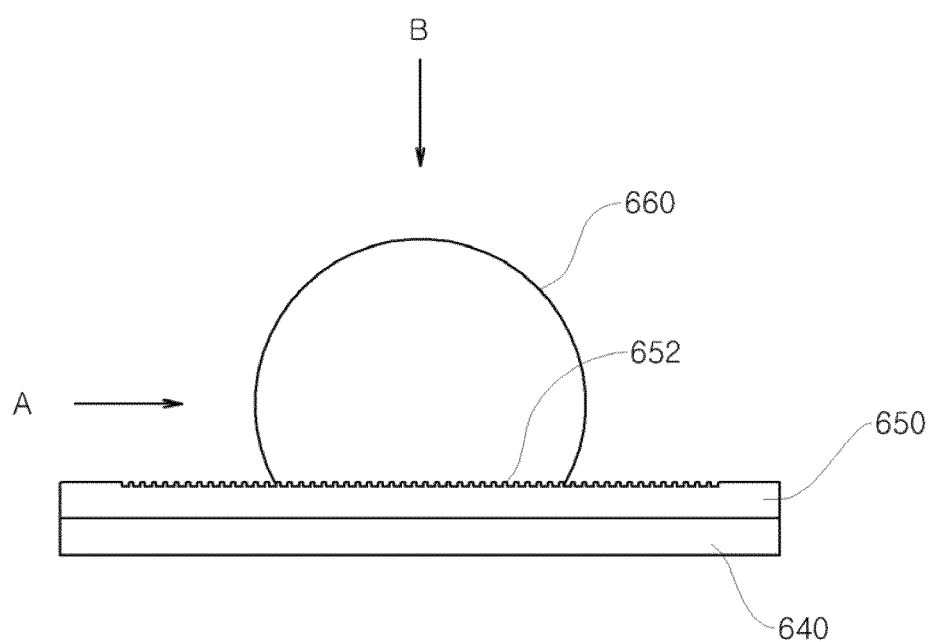
FIG. 6 is a partial cross-sectional view of a pressure sensor according to another exemplary embodiment of the present disclosure.

FIG. 6 is a partial cross-sectional view of a pressure sensor according to another exemplary embodiment of the present disclosure.

Referring to FIG. 6, a nanostructure 650 having a plurality of wrinkles is attached on a flexible sensor layer 640 and then a dome structure 660 is attached on the nanostructure 650. Although the number of the dome structure 660 is one in FIG. 6, two or more dome structures may be attached by varying the size of the dome structure.

The dome structure 660 may maximize transfer and sensing of shear stress A and normal pressure B due to its convex shape. The dome structure 660 may comprise PDMS, PMMA, SU8, PU, parylene or elastomer.

Figure 7:
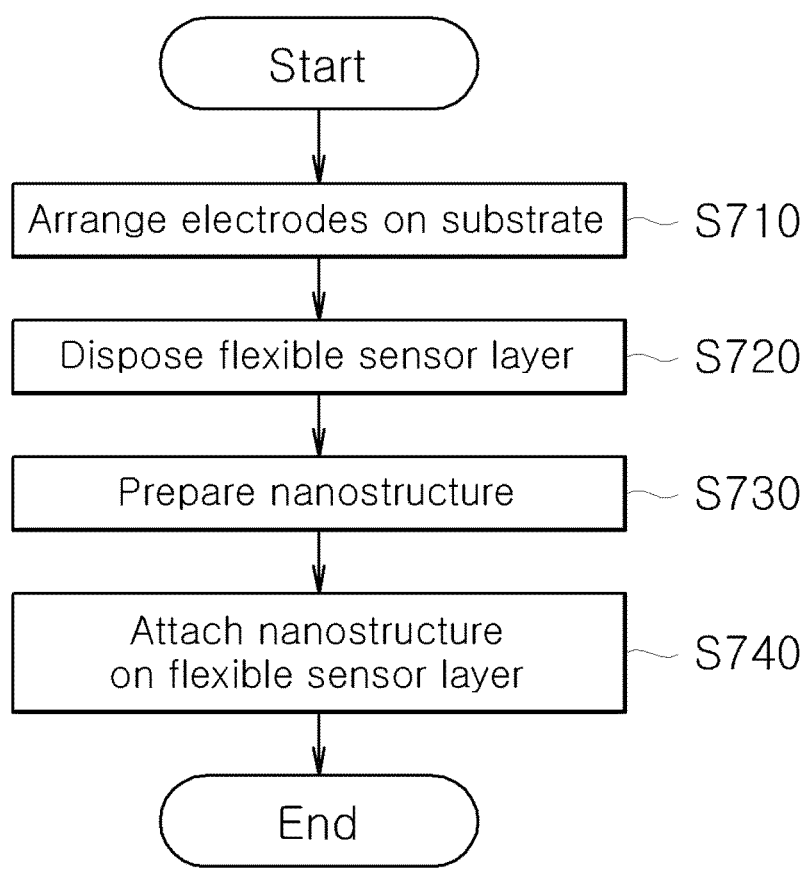
FIG. 7 is a flow chart illustrating a method for manufacturing a pressure sensor according to an exemplary embodiment of the present disclosure.

FIG. 7 is a flow chart illustrating a method for manufacturing a pressure sensor according to an exemplary embodiment of the present disclosure.

Referring to FIG. 7, a source electrode 120 and a drain electrode 130 are arranged first on a substrate 110 (S710). Then, a flexible sensor layer 140 is disposed on the source electrode 120 and the drain electrode 130 (S720).

Subsequently, a nanostructure 150, 250, 350, 360 is prepared by forming nanosized wrinkles on a thin film of a polymer material as illustrated in FIGS. 2b-2e (S730), and the nanostructure 150, 250, 350, 360 having wrinkles is attached on the flexible sensor layer 140 (S740).

Alternatively, the nanostructure 150, 250, 350, 360 may be prepared prior to S710 and S720 and attached on the flexible sensor layer 140.

In an exemplary embodiment of the present disclosure, the nanostructure is a linear 1-dimensional structure as shown in FIG. 2b. To prepare the nanostructure, while applying tension to a thin film 410, a mask 420, 430 may be disposed on the thin film and UV ozone or $O_2$ plasma may be applied to modify the surface selectively exposed by the mask so as to form wrinkles using the difference in stress between the modified surface and the unmodified surface, as illustrated referring to FIGS. 3a-3b. Alternatively, tension and UVO may be applied onto a thin film 510 having portions 510a, 510b, 510c with different thickness so as to form wrinkles on a relatively thin portion 510b, as illustrated referring to FIGS. 4a-4c.

In another exemplary embodiment of the present disclosure, the nanostructure is a zigzag-shaped 2-dimensional structure as shown in FIG. 2c and the structure is formed by buckling. That is to say, after depositing a nano-linewidth metal thin film or metal oxide thin film having external tension, usually tensile strength, on a thin film of a polymer material, the metal thin film or the metal oxide thin film may be artificially removed to generate local stress, thus forming wrinkles.

In another exemplary embodiment of the present disclosure, the nanostructure is a spiral-shaped structure as shown in FIG. 2d or FIG. 2e and the structure is formed by wrinkling or buckling.

To describe in detail, after applying tensile strength to a thin film 610, the portion except for the portion where the wrinkles will be formed is masked using a PET film 620 or a photoresist, the surface is modified using UVO and the tensile strength is removed to form nanowrinkles, as illustrated referring to FIG. 5. As the surface of the thin film 610 is exposed to UVO by a spiral-shaped through-hole 622 of the PET film 620, the nanowrinkles having a shape corresponding to the spiral-shaped through-hole 622 are formed.

Alternatively, after masking the thin film 610 with the PET film 620 or the photoresist, a nano-linewidth metal thin film or metal oxide thin film having external tension, usually tensile strength, may be artificially deposited on the thin film 610 and then the metal thin film or the metal oxide thin film may be artificially removed to generate local stress, thus forming wrinkles.

After the nanostructure having wrinkles is attached on the flexible sensor layer 140 (S740), a process of forming a nano-sized dome structure 660 and attaching it on the nanostructure having wrinkles may be further included.

The dome structure 660 may be attached onto one or more nanostructure and may further improve the response time and sensitivity of the sensor in 3-dimensional x-y-z directions.

The pressure sensor and the method for manufacturing the same according to the present disclosure may provide improved sensor response time and sensitivity because of the nanostructure attached on the surface of the sensor.

Also, the pressure sensor and the method for manufacturing the same according to the present disclosure may prevent degradation of viscoelastic property when the thickness of the flexible sensor layer is decreased by disposing a nanostructure on the surface of the flexible sensor layer.

While the present disclosure has been described with respect to the specific embodiments, it will be apparent to those skilled in the art that various changes and modifications may be made without departing from the spirit and scope of the disclosure as defined in the following claims.

What is claimed is:

1. A method for manufacturing a pressure sensor comprising:
    a substrate;
    a source electrode and a drain electrode on the substrate with a predetermined spacing;
    a flexible sensor layer disposed on the source electrode and the drain electrode;
    a nanostructure attached on the surface of the flexible sensor layer and comprising nanosized wrinkles that transfer normal pressure to the flexible sensor layer; and
    a dome structure attached on the surface of the nanostructure to maximizes pressure sensing in a 3-dimensional direction, the method comprising:
    arranging the source electrode and the drain electrode on the substrate;
    disposing a flexible sensor layer on the source electrode and the drain electrode;
    forming nanosized wrinkles on a thin film of a polymer material to prepare a nanostructure;
    attaching the nanostructure having wrinkles on the surface of the flexible sensor layer; and
    forming a nanosized dome structure and attaching it on the nanostructure having wrinkles.

2. The method for manufacturing a pressure sensor according to claim 1, wherein said preparing the nanostructure comprises forming a linear 1-dimensional structure.

3. The method for manufacturing a pressure sensor according to claim 2, wherein said forming the linear 1-dimensional structure comprises forming wrinkles by disposing a mask on the thin film, applying UV ozone (UVO) or $O_2$ plasma to modify the surface selectively exposed by the mask and forming wrinkles using the difference in stress between the modified surface and the unmodified surface, while applying tension to the thin film.

4. The method for manufacturing a pressure sensor according to claim 2, wherein said forming the linear 1-dimensional structure comprises forming wrinkles on the portion of the thin film having a relatively smaller thickness by applying tension and UV ozone (UVO).

5. The method for manufacturing a pressure sensor according to claim 1, wherein said preparing the nanostructure comprises forming a zigzag-shaped 2-dimensional structure.

6. The method for manufacturing a pressure sensor according to claim 5, wherein said forming the zigzag-shaped 2-dimensional structure comprises artificially depositing a nano-linewidth metal thin film or metal oxide thin film having tensile strength on the thin film of a polymer material and artificially removing the metal thin film or the metal oxide thin film to generate local stress, thus forming wrinkles.

7. The method for manufacturing a pressure sensor according to claim 1, wherein said preparing the nanostructure comprises forming a spiral-shaped structure.

8. The method for manufacturing a pressure sensor according to claim 7, wherein said forming the spiral-shaped structure comprises applying tensile strength to both ends of the thin film, masking the portion except for the portion where wrinkles will be formed using a PET film or a photoresist, modifying the surface using UV ozone (UVO) and removing the tensile strength applied to the thin film to form the wrinkles.

9. The method for manufacturing a pressure sensor according to claim 7, wherein said forming the spiral-shaped structure comprises masking the thin film with a PET film or a photoresist, artificially depositing a nano-linewidth metal thin film or metal oxide thin film having tensile strength on the thin film and artificially removing the metal thin film or the metal oxide thin film to generate local stress, thus forming wrinkles.

\* \* \* \* \*